United States Patent
Tolvanen et al.

Patent Number: 5,715,046
Date of Patent: Feb. 3, 1998

[54] PROCESS AND DEVICE FOR OIL STABILITY MEASUREMENT

[75] Inventors: Ilkka Tolvanen, Saksala; Jürg Waldvogel, Porvoo; Olli Pilviö, Söderkulla, all of Finland

[73] Assignee: Neste Oy, Espoo, Finland

[21] Appl. No.: 663,105
[22] PCT Filed: Dec. 21, 1994
[86] PCT No.: PCT/FI94/00575
§ 371 Date: Jul. 15, 1996
§ 102(e) Date: Jul. 15, 1996
[87] PCT Pub. No.: WO95/18367
PCT Pub. Date: Jul. 6, 1995

[30] Foreign Application Priority Data
Dec. 31, 1993 [FI] Finland ............ 935973

[51] Int. Cl.$^6$ ............ G01N 33/28; G01N 21/41
[52] U.S. Cl. ............ 356/70; 356/134
[58] Field of Search ............ 356/70, 73, 436, 356/437, 440; 250/343, 227, 573, 577; 422/69, 68, 70; 210/658, 198; 436/162, 60, 2, 140, 141, 161

[56] References Cited

U.S. PATENT DOCUMENTS

| | | | |
|---|---|---|---|
| 4,352,983 | 10/1982 | Silvus, Jr. et al. | 250/227 |
| 4,588,297 | 5/1986 | Inazaki et al. | 356/376 |
| 4,628,204 | 12/1986 | Maes | 250/343 |
| 4,649,281 | 3/1987 | Schmitt et al. | 250/574 |
| 4,659,218 | 4/1987 | de Lasa et al. | 356/133 |
| 4,677,304 | 6/1987 | Camp et al. | 250/577 |
| 4,781,892 | 11/1988 | Dickakian | 422/69 |
| 4,843,247 | 6/1989 | Yamazoe et al. | 250/573 |
| 4,929,847 | 5/1990 | Yamazoe et al. | 250/573 |
| 4,934,818 | 6/1990 | Glantschnig et al. | 356/73 |
| 4,940,900 | 7/1990 | Lambert | 250/343 |
| 5,420,040 | 5/1995 | Anfindsen et al. | 436/60 |

FOREIGN PATENT DOCUMENTS

| | | |
|---|---|---|
| 0551145 | 7/1993 | European Pat. Off. |
| 2097529 | 11/1982 | United Kingdom. |
| 2217838 | 11/1989 | United Kingdom. |

Primary Examiner—Frank G. Font
Assistant Examiner—Michael P. Stafira
Attorney, Agent, or Firm—Birch, Stewart, Kolasch and Birch, L.L.P.

[57] ABSTRACT

A method and a device for determination of the stability or storability of oil, wherein the stability of oil is determined by measuring the intensity of light scattering from the oil surface, when an asphalteneflocculating liquid is added to the oil sample for determining the stability of the oil. In an advantageous embodiment of the method the intensity of scattered light is directed onto the surface of the oil sample by using a suitable prism. The invention allows implementation of a fully automatically operating analyzer for determining the stability of oil. A closed measuring system is brought about that solves the explosion protection problem which is important in oil refining.

11 Claims, 3 Drawing Sheets

PROCESS AND DEVICE FOR OIL STABILITY MEASUREMENT

BACKGROUND OF THE INVENTION

1. Field of the Invention

The invention concerns a method and a device for determination of the stability or storability of oil.

2. Description of the Related Art

Oil refining gives rise to dark heavy high-boiling oil fractions and their mixtures, of which bitumen and heavy fuel oil are made, among other things. The use and storability of these oil raffinates are impaired by the poor solubility or precipitation of asphaltenes in the oil. The precipitation ability of asphaltenes determines the stability or storability of the oil, and this dpenends both on the oil production process used and on the raw materials. In particular, the heat-cracking unit which is used today affects the precipitation ability of asphaltenes. Hereby the oil refining process should be controlled so that the heavy fuel oil obtained as the basis product of the unit will be stable.

The stability of oil has traditionally been determined from samples taken from the oil, i.a. by so-called flocculation methods (for example, the Shell method; Flocculation ratio of bitumen and fuel oil). These methods are based on paper chromatography and on visual perceptions in this connection. Getting a result takes from ½ to 6 hours when using this method.

Automatic on-line analyzers have been developed which are based, for example, on an observation of the oil product's asphaltene content either in connection with the production process or on a measurement of laboratory samples.

In an automatic on-line analyzer of this type a computer-controlled process analyzer automatically takes a samples from the desired product flow at determined intervals and put out a parameter indicating the stability to the process control room at determined intervals of time, for example, 10 minutes.

However, in these methods it has been a problem that the measurement results are too varied or the measurement methods have been too slow for adjusting the process.

Another problem with the known methods is that the measuring cell used for measuring has been open. As measurements can not be done in a closed measuring system, handling of the sample has been cumbersome and protection against explosion, which is very important in oil refining, has been problematic.

The invention aims at bringing about an improvement in the known methods of determining the stability or storability of oil. A more closely specified aim of the invention is to bring about a method of determining the stability of oil directly from the oil surface, so that the obtained measurement result can be used in controlling the oil quality or in controlling the production.

SUMMARY OF THE INVENTION

It is an objective of the invention to bring about a method allowing a fully automatically operating analyzer for determining the stability of oil.

An other objective of the invention is to bring about a closed measurement system. In a closed measurement system separate sample handling is avoided and the problem of protection against explosions, which is very important in oil refining, has been solved.

The above-mentioned objectives are achieved through a new method and device, which are characterized by the features presented in the independent patent claims.

The invention is based on the surprising finding that the stability of oils can be determined promptly and reliably by measuring the intensity of light scattering from the oil surface.

It was also found surprisingly that by designing the analyzer's measuring cell for oil stability measurement so that measuring takes place through a prism, the drawbacks of methods representing the ate of the an could be avoided.

Several advantages are obtained by using a prism in a measuring device in accordance with the invention. Using the prism it is possible to direct the light ray arriving in the studied oil sample directly to the desired point without any harmful reflections. Likewise, the desired part of the light leaving the oil sample can be directed to an indicator. When a prism is used there is no open oil sample surface in the measuring device, so the measuring device can be entirely close.

When using the method according to the invention for measuring the stability of heavy oil fractions derived from petroleum or the stability of their mixtures, a diluent such as, for example, toluene, xylene or some other diluent may be added to the oil and at the same time or afterwards, asphaltene-flocculating hydrocarbon is added to the oil, such as pentane, hexane, heptane, octane or some other, until the intensity of the scattering light ray increases sharply, thus indicating the flocculation point of the asphsltene. The stability of the oil being measured can be calculated with one or several determinations and expressed with a figure indicating the stability, for example, as xylene equivalents.

The method now developed makes possible an optical determination of the stability of oil from the oil surface. The remit call be used for controlling the oil production or for quality monitoring. An analyzer functioning with the method according to the invention can be fully automated even for sampling and result computing, which allows the important use of a quality magnitude in the automatic follow-up of the oil production and in the process control.

BRIEF DESCRIPTION OF THE DRAWINGS

The invention is explained in greater detail by referring to the principal solution of the method according to the invention, which is shown in the figure in the enclosed drawing, but to which the invention is not intended to be limited.

FIG 1 shows a measurement of the stability of oil based on light scarring. Reference number 10 in the figure indicates the measuring device in general. The measuring device 10 comprises a light source 11, a sample vessel 12, in indicator 14 and equipment 15 feeding a diluent or flocculating additive. A light ray 16 is directed at any angle from light source 11 onto the surface of oil 13 in sample vessel 12, whereby a part of the arriving light ray 16 is reflected as a light ray 17 reflected from the oil surface and a part is scarred as a light my 18 scattered from the oil surface and from the particles it contains, which latter light ray is detected by indicator 14 at any angle. When measuring the stability of oil a flocculating additive is supplied into sample vessel 12 from feeding equipment 15.

The monochromatic light ray 16 and the normal 19 to the surface of oil sample 13 form an angle α of any value. The light ray 18 scattered from the oil surface and the normal 19 to the surface of oil sample 13 form an angle α of any value.

Figure 1:
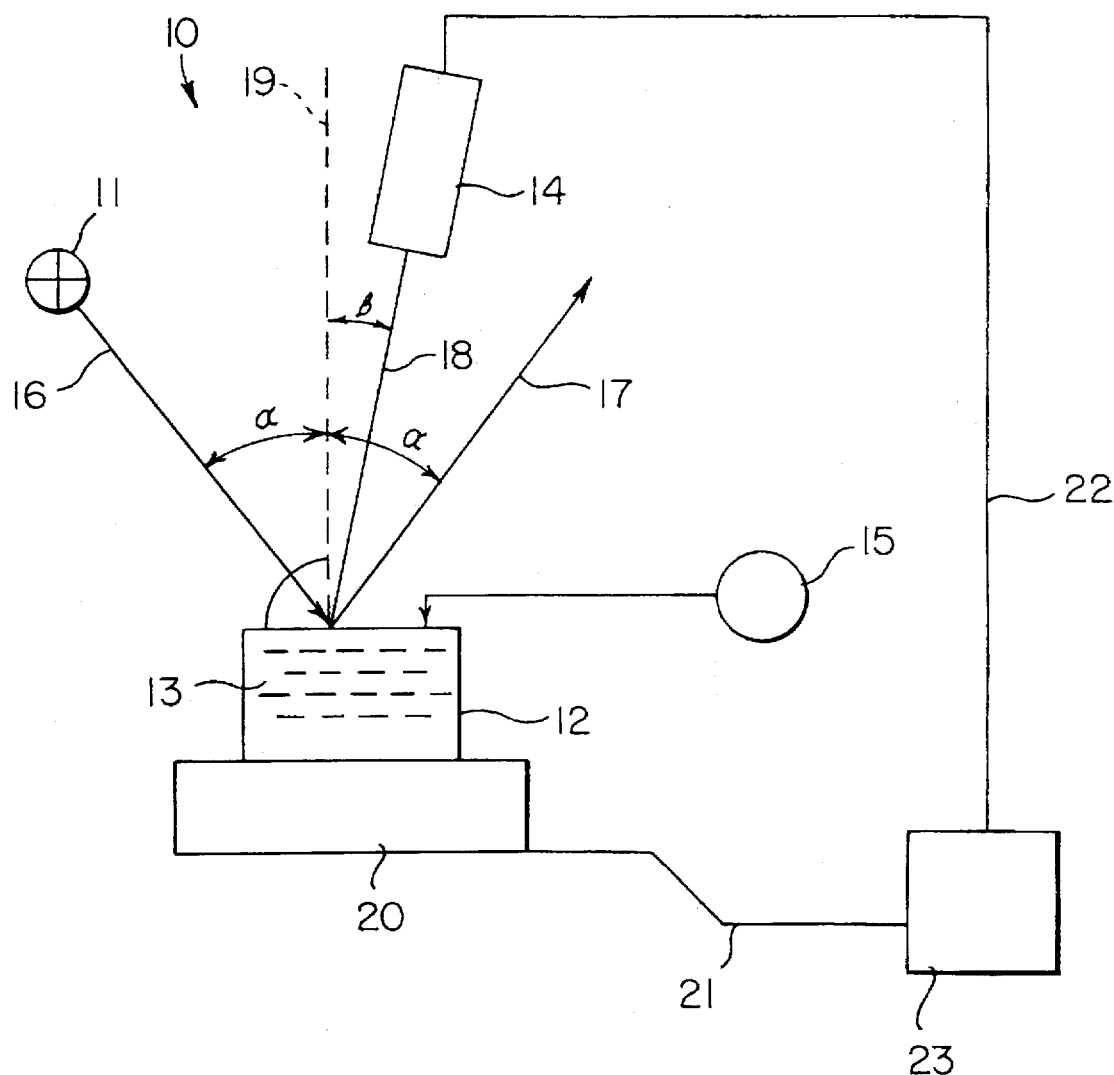
FIG. 1. Measurement of oil stability based on light scattering.

When measuring device 10 according to FIG. 1 is used for measuring the stability of heavy oil fractions derived from petroleum or the stability of their mixtures, a diluent, such as toluene, xylene or some other similar diluent is preferably though not necessarily added to the oil in sample vessel 12. Then asphaltene-flocculating hydrocarbon, for example, pentane, heptane, octane or some similar is supplied from feeding equipment 15 and measures by balance 20 into sample vessel 12, until the intensity of the scattered light 18 rises sharply, thus indicating the flocculation point of the asphaltene. The stability is calculated with the aid of one of several determinations and it is expressed, for example, as xylene equivalents, known previously as a measure of stability.

When the method in accordance with the invention is used for measuring contents of substances insoluble in heavy oil fractions derived from petroleum or in their mixtures, the arriving light my 16 is directed onto the oil produce surface and onto the oil layer under the surface, whereby the intensity of light 18 scattered from the oil product surface and from inside the oil product will indicate the content of particles in the oil.

Figure 2:
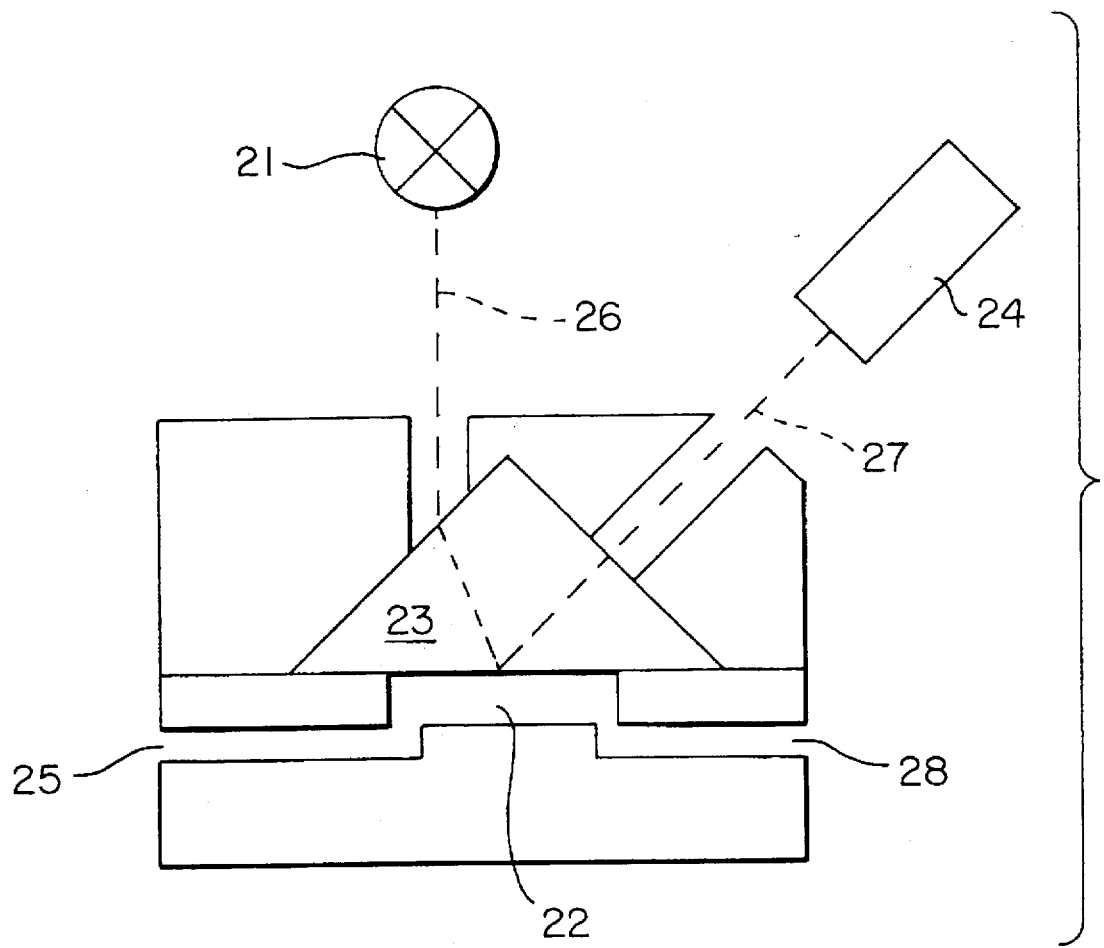
FIG. 2. Measurement of oil stability based on light scattering and using a prism.

FIG. 2 shows a measurement of the stability of oil based on light scattering and using a prism. The measuring device comprises a light source 21, a sample chamber 22, an indicator 24 and feeding channels 25 for supplying oil and a additive. The light my 26 arriving from light source 21 hits the prism 23, thus being directed from its surface onto the interface of the prism and the sample to be examined, from which interface part of the light is scattered as a reflected light ray 27 to indicator 24.

As in the device shown in FIG. 1, the measuring device is also associated with a piece of equipment, wherein a diluent or a flocculating additive is added to the oil to be examined. This mixture is supplied through feeding channel 25 into the sample and further to leave the measuring device by way of exhaust channel 28.

Figure 3:
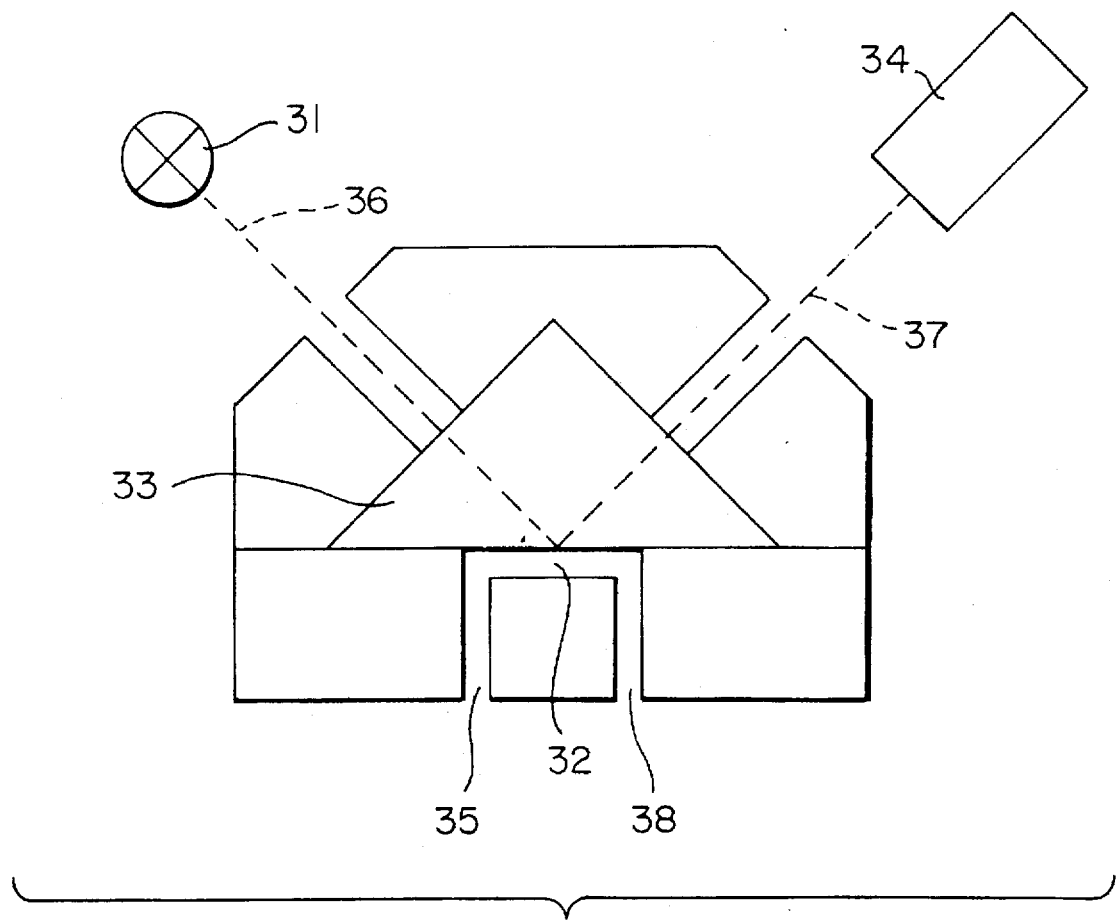
FIG. 3. Measurement of oil stability based on light reflection and using a prism.

FIG. 3 shows a measurement of the stability of oil based on light reflection and using a prism. The measuring device comprises a light source 31, a sample chamber 32, a prism 33 having a 90° angle facing the sample chamber 32, an indicator 34, feeding channels 35 and exhaust channels 38 for feeding oil and a diluent or a flocculating additive. Light ray 36 arriving from light source 31 hits prism 33, passing from its surface onto the interface of the prism and the sample to be examined, from which interface part of the light is reflected as a light ray 37 to the indicator 34.

This measuring device, too, like the device in accordance with FIGS. 1 and 2, may be associated with a piece of equipment wherein a diluent or a flocculating additive is added to the oil being examined. This mixture is fed through feeding channel 35 into the sample chamber and further to leave the measuring device by way of exhaust channel 38.

We claim:

1. Method of determining the stability oil, comprising:
   adding diluents and asphaltene-flocculating agents to an oil sample until the flocculation point of asphaltenes is reached;
   using a suitable prism to direct a first light ray from a light source onto the surface of the oil sample, wherein said sample is in a closed space formed in part by a side wall of said prism; and
   measuring the intensity of a second light ray scattered or reflected from the surface of the sample, whereby a sharp increase in the intensity of the second light ray indicates the flocculation point of the asphaltenes.

2. Method as defined in claim 1, wherein the angle of the prism facing the sample chamber is 90°.

3. Method in accordance with claim 1, characterized in that when determining the stability of oil, especially of heavy oil fractions derived from petroleum or of their mixtures, an asphaltene-flocculating liquid is added to the oil sample.

4. Method as defined in claim 3, characterized in that pentane, hexane, heptane, octane or any liquid having similar properties is used as the liquid for flocculating asphaltenes.

5. Method as defined in claim 1, characterized in that when determining the stability parameter or xylene equivalent of oil, especially of heavy oil fractions derived from petroleum or of their mixtures, toluene, xylene or some similar diluent is used and it is added before or simultaneously with the flocculating liquid.

6. Method as defined in claim 1, characterized in that the oil sample is agitated during the determination.

7. A device for determining the stability of oil, characterized in that the device has a light source which produces a first light ray, a prism for directing the first light ray onto the surface of the oil sample being examined, a sample vessel containing an oil sample from which a second light ray is scattered or reflected, and an indicator for measuring the light intensity, wherein said sample vessel defines a closed space formed in part by a side wall of said prism.

8. Device as defined in claim 7, wherein said prism transmits the second light ray which is reflected or scattered from the surface of the oil sample.

9. Method of determining the stabiility of oil comprising:
   adding diluents and asphaltene-flocculating agents to an oil sample until the flocculation point of asphaltenes is reached;
   using a suitable prism to direct a first light ray from a light source onto the surface of the oil sample, wherein said sample is in a closed space; and
   measuring the intensity of a second light ray which is scattered or reflected from the surface of the sample, whereby a sharp increase in the intensity of the second light ray indicates the flocculation point of the asphaltenes, and wherein said prism transmits the second light ray which is scattered or reflected from the surface of the sample.

10. Method as defined in claim 1, wherein the prism transmits the light ray which is reflected or scattered from the surface of the sample.

11. Method as defined in claim 9, wherein said closed space is formed in part by a side wall of said prism.

* * * * *